(12) United States Patent
Salvatelli et al.

(10) Patent No.: US 11,679,015 B2
(45) Date of Patent: Jun. 20, 2023

(54) OFF-LOAD HIGH LEG-FOOT BRACE

(71) Applicant: SALVATELLI S.R.L, Civitanova Marche (IT)

(72) Inventors: Susanna Salvatelli, Civitanova Marche (IT); Franco Salvatelli, Civitanova Marche (IT); Alberto Salvatelli, Potenza Picena (IT)

( * ) Notice: Subject to any disclaimer, the term of this patent is extended or adjusted under 35 U.S.C. 154(b) by 491 days.

(21) Appl. No.: 15/573,764

(22) PCT Filed: Dec. 29, 2015

(86) PCT No.: PCT/EP2015/081375
§ 371 (c)(1),
(2) Date: Nov. 13, 2017

(87) PCT Pub. No.: WO2016/184533
PCT Pub. Date: Nov. 24, 2016

(65) Prior Publication Data
US 2018/0104081 A1 Apr. 19, 2018

(30) Foreign Application Priority Data
May 15, 2015 (IT) .......................... 102015000015397

(51) Int. Cl.
*A61F 5/01* (2006.01)
*A43B 7/1464* (2022.01)
*A43B 7/22* (2006.01)

(52) U.S. Cl.
CPC .......... *A61F 5/0111* (2013.01); *A61F 5/0195* (2013.01); *A43B 7/1464* (2022.01); *A43B 7/22* (2013.01)

(58) Field of Classification Search
CPC ....... A43B 3/0047; A43B 7/00; A43B 7/1405; A43B 7/141; A43B 7/1465; A43B 7/22; A43B 7/226; A43B 7/30; A43B 23/00; A43B 21/37; A43B 21/39; A43B 7/10; A43B 7/12; A43B 7/122; A43B 7/125; A43B 7/127; A43B 7/14; A61F 5/01; A61F 5/0102; A61F 5/0127; A61F 5/0111; A61F 5/0113; A61F 5/0195; A61F 5/0585; A42B 7/1464; A42B 7/22
USPC ........................... 602/13, 23, 27, 28, 29, 65
See application file for complete search history.

(56) References Cited

U.S. PATENT DOCUMENTS

| | | | | |
|---|---|---|---|---|
| 4,572,169 A | * | 2/1986 | Mauldin | A61F 5/0111 602/27 |
| 5,735,805 A | * | 4/1998 | Wasserman | A61F 5/0111 36/15 |
| 5,896,684 A | * | 4/1999 | Lin | A43B 3/103 36/101 |
| 5,961,477 A | * | 10/1999 | Turtzo | A61F 5/0111 602/12 |

(Continued)

*Primary Examiner* — Rachael E Bredefeld
*Assistant Examiner* — Seth R. Brown
(74) *Attorney, Agent, or Firm* — Egbert, McDaniel & Swartz, PLLC

(57) ABSTRACT

A brace includes a bottom having a sole made of a soft material with a tread intended to come in contact with the ground, and a stiffening plate fixed on the sole. A rigid body is provided having a base plate removably connected to the stiffening plate. A monolithic upper is removably connected to the body, and at least one intermediate sole made of a soft material is disposed on the base plate of the body.

11 Claims, 4 Drawing Sheets

(56) References Cited

U.S. PATENT DOCUMENTS

| | | | | |
|---|---|---|---|---|
| 6,302,858 | B1* | 10/2001 | DeToro | A61F 5/0111 |
| | | | | 602/23 |
| 6,464,659 | B1* | 10/2002 | DeToro | A61F 5/0195 |
| | | | | 602/23 |
| 8,230,619 | B2* | 7/2012 | Salvatelli | A43B 7/1465 |
| | | | | 36/88 |
| 2001/0049484 | A1* | 12/2001 | Lamont | A61F 5/34 |
| | | | | 602/3 |
| 2003/0046829 | A1* | 3/2003 | Baechtold | A63C 9/086 |
| | | | | 36/15 |
| 2006/0196086 | A1* | 9/2006 | Sellers | A43B 13/143 |
| | | | | 36/132 |
| 2007/0191749 | A1* | 8/2007 | Barberio | A43B 7/20 |
| | | | | 602/23 |
| 2016/0235578 | A1* | 8/2016 | Romo | A61F 5/0195 |

* cited by examiner

OFF-LOAD HIGH LEG-FOOT BRACE

The present patent application for industrial invention relates to an off-load high leg-foot brace capable of immobilizing the foot and the leg of a patient, either completely or partially.

Orthopedic braces can be found on the market, comprising a suitably shaped s sole in order to allow the patient wearing said orthopedic braces to walk without stressing the injured foot.

U.S. Pat. No. 8,230,619 discloses an orthopedic footwear comprising an ambidextrous bottom sole comprising a large groove that is open on top and extends for almost the entire length and width of the sole. Said groove is intended to receive a rigid insert having a function of avoiding flexing and torsion in the plantar area of the foot both in a static and dynamic phase.

The rigid insert has an upper surface intended to be faced towards the plantar area of the patient's foot, which is perfectly smooth and flat.

The orthopedic footwear described in document U.S. Pat. No. 8,230,619 also comprises an upper directly and firmly connected to the bottom sole and a soft insole disposed on the rigid insert. The soft insole is of modular type and is composed of three interchangeable modules having different elasticity.

In spite of the aforementioned advantages, the use of similar orthopedic footwear is impaired by the fact that, during deambulation, the portion of the upper disposed in correspondence of the portion of the foot comprised between the heel and the calcaneus tends to bend with consequent discomfort for the patient.

In said orthopedic footwear of the prior art, the upper padding has a negative effect on deambulation and is hardly accepted by the patient.

It must be noted that the portion of the upper disposed in correspondence of the portion of the foot comprised between the heel and the calcaneus must be constantly inclined by an angle of 90° with respect to the upper flat surface of the rigid insert so that the patient can deambulate comfortably while keeping the foot in its correct position.

In the orthopedic footwear of the prior art, the upper and the shape of the bottom sole are designed from time to time according to the specific therapy and/or s pathology of the patient's foot; in view of the above, according to the patient's therapy and/or pathology, it is necessary to purchase a specific model of orthopedic footwear.

The purpose of the present invention is to remedy the aforementioned drawbacks of the prior art by disclosing an off-load high leg-foot brace that, in spite of being produced in a standard version, can be modified and customized during use according to the patient's foot and therapy/pathology.

The off-load high leg-foot brace of the invention comprises:
- a bottom comprising a sole, made of soft material, comprising a tread intended to come in contact with the ground, and a stiffening plate made of a hard is indeformable material that is associated with the sole and fixed thereon,
- a rigid body comprising a base plate removably connected to the stiffening plate,
- a monolithic upper removably connected to the body, and
- at least one intermediate sole made of soft material disposed on the base plate of the body.

The advantages of the brace according to the present invention are evident, it comprising an upper that, in case of need, can be easily and rapidly replaced with another upper according to the patient's requirements.

Moreover, the upper of the brace of the invention is made of a material that can be thermoformed and cut according to the shape of the foot and to the injuries of the patient, in order to perfectly adjust to the foot and the pathology of the patient's foot.

It should not be forgotten that also the bottom, which is composed of the aforementioned soft sole and stiffening plate, can be easily coupled and uncoupled with respect to the body of the brace of the invention in such manner that the patient can provide the brace with a suitable bottom from time to time according to his pathology and medical conditions, given the fact that, in spite of being always provided with the stiffening plate that is to be connected to the body, the bottom can be characterized by a sole with different softness level and a tread with a different curvilinear profile.

For purpose of clarity the description of the brace according to the present invention continues with reference to the attached drawings, which are intended for purposes of illustration only, and not in a limiting sense, wherein:

FIG. 6 is a side view of the bottom of the brace according to the invention, wherein the sole in shown in a second embodiment.

Figure 1:
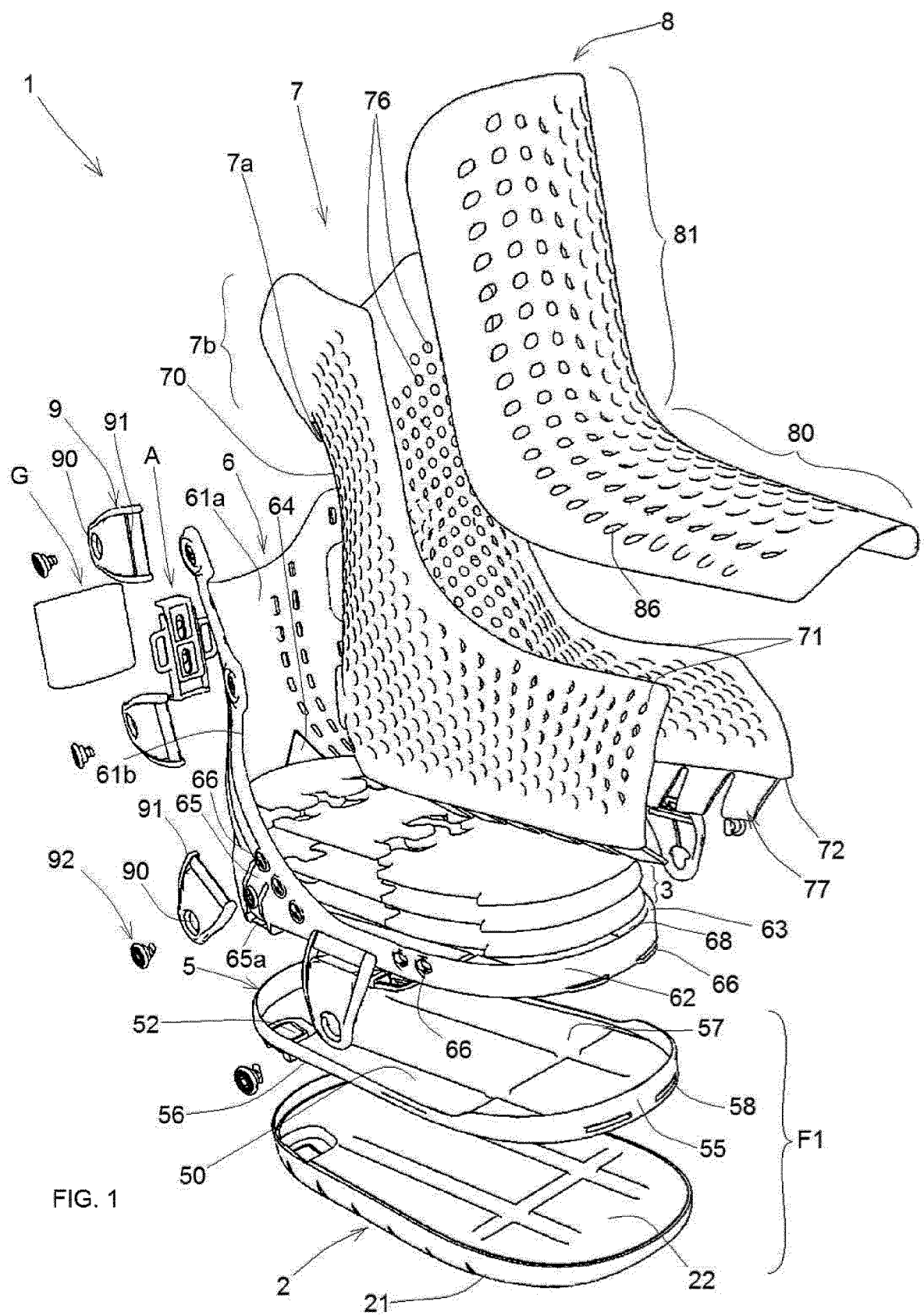
FIG. 1 is an exploded axonometric view of the parts of the brace according to the invention.

With reference to the attached figures, the brace of the invention is disclosed and generally indicated with reference numeral (1).

Figure 2:
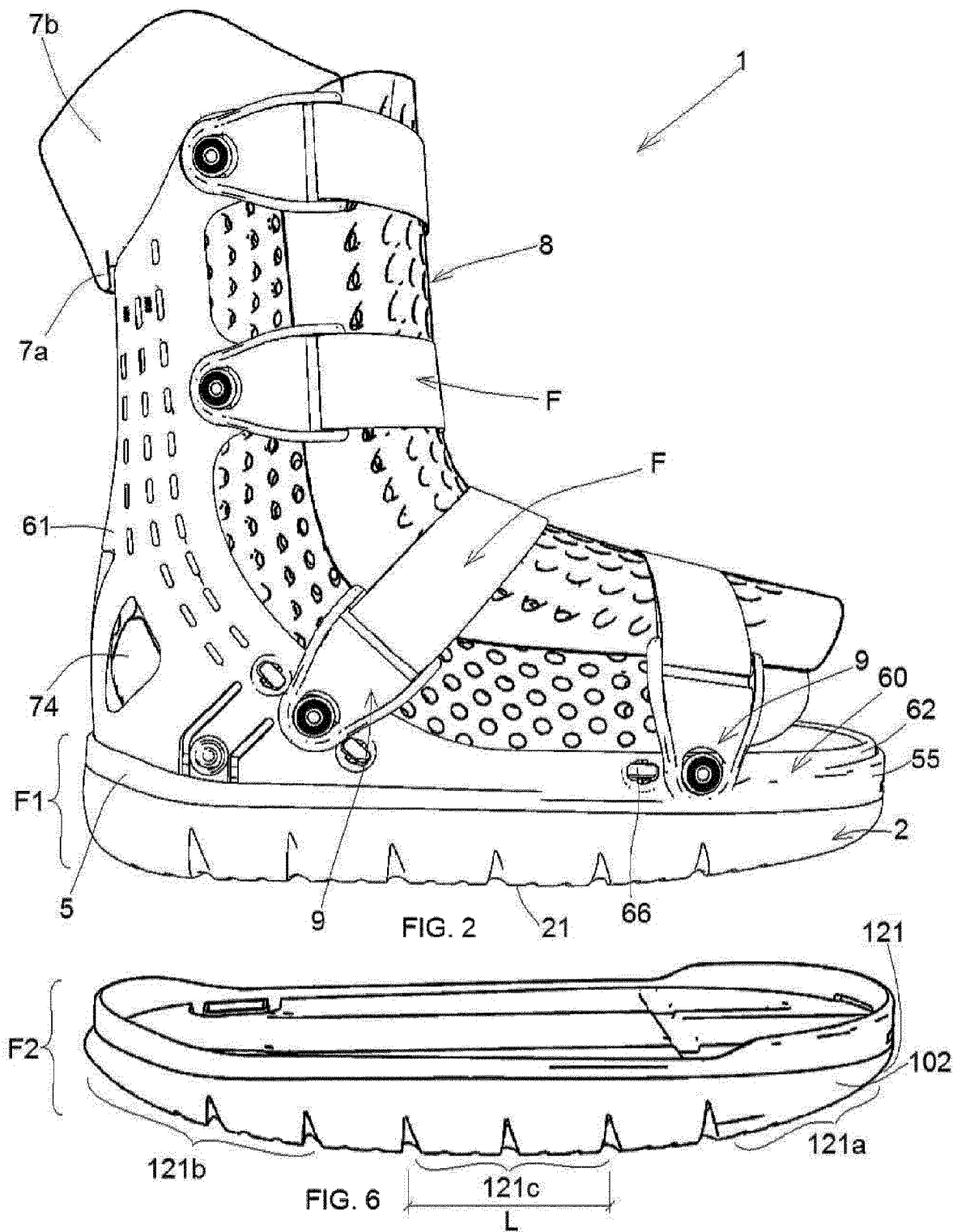
FIG. 2 is a side view of the brace of the invention, in assembled condition.

With special reference to FIGS. 1 and 2, the brace (1) comprises a bottom (F1) comprising a soft sole (2) and a stiffening plate (5) associated with the sole (2) and fixed on the sole (2).

The sole (2) comprises a tread (21) intended to come in contact with the ground, and an internal surface (22) intended to be faced towards the patient's foot.

In the description below, the terms "front" and "back" are referred respectively to the tip of the foot and the heel.

The sole (2) is obtained from molding a soft thermoformable material, such as soft thermoplastic polyurethane or soft ethylene vinyl acetate (EVA).

Figure 3:
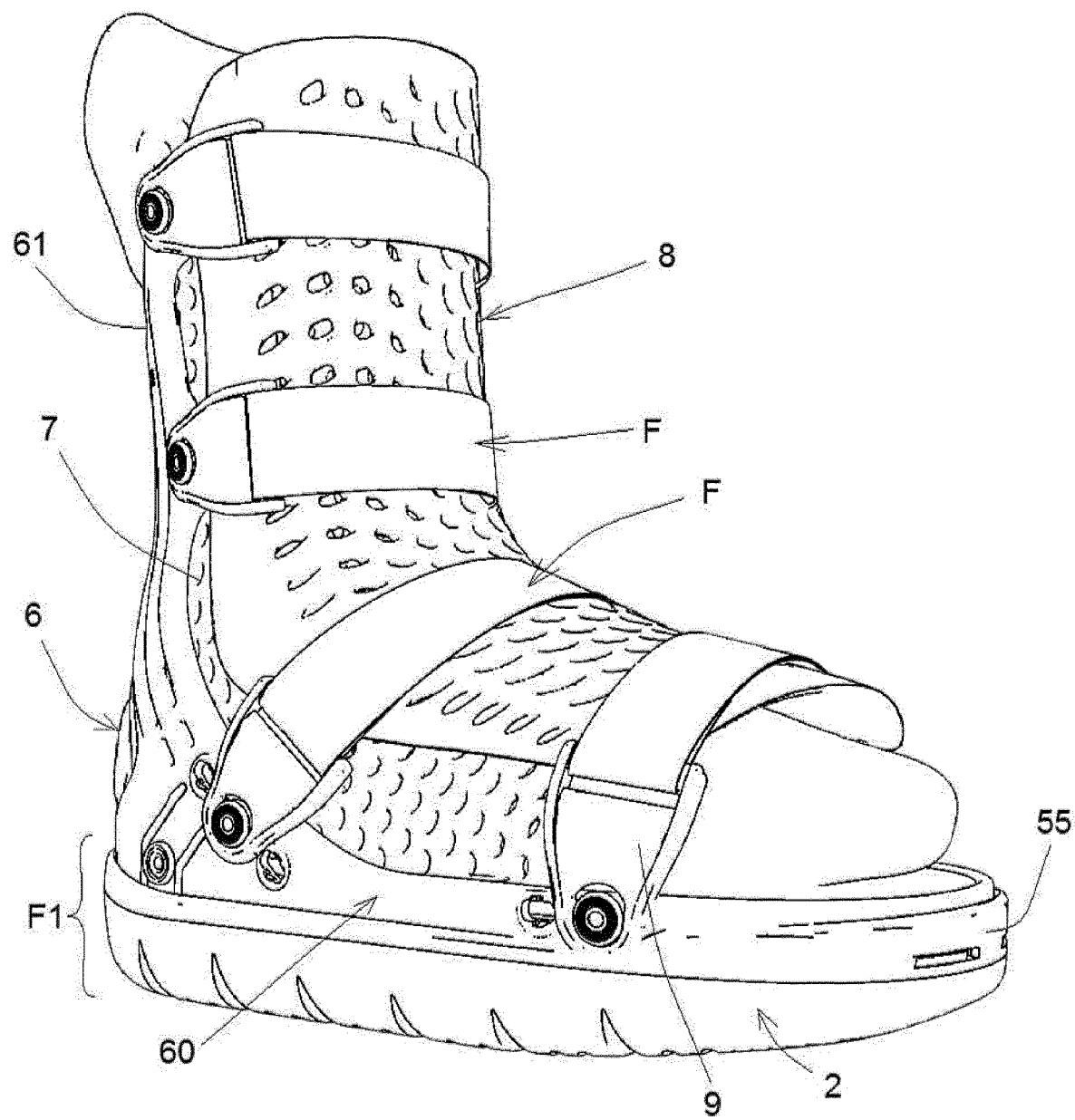
FIG. 3 is an axonometric view of the brace of the invention, in assembled condition.

With reference to FIGS. 2 and 3, the stiffening plate (5) of the brace (1) is rigid and indeformable and has a shape similar to the internal surface (22) of the sole. The stiffening plate (5) comprises a lower surface (56) that is faced towards the sole (2), and an upper surface (57) that is faced upwards. The stiffening plate (5) is made of a rigid material, preferably rigid polyurethane.

The stiffening plate (5) is glued to the sole (2) in order to increase the hardness and the rigidity of the surface whereon the patient's foot rests, and avoid flexing the sole (2) longitudinally during deambulation.

The stiffening plate (5) has a perimeter edge (55) that protrudes upwards from the upper surface (57) of the stiffening plate, defining a cavity (50) that is open on top and extends for the entire length and width of the stiffening plate (5).

With reference to FIG. 1, the stiffening plate (5) is provided with two front slots (58) obtained in the front part on the perimeter edge (55) of the stiffening plate.

The stiffening plate (5) is also provided with two back slots (52) obtained in peripheral position on the back of the upper surface (57) of the stiffening plate.

The brace (1) comprises a body (6) made of rigid plastic, preferably rigid polypropylene. The body (6) is connected to the stiffening plate (5) by means of snap-fit coupling.

The body (6) is provided with an L-shaped configuration in cross-sectional view and comprises a base plate (60) and a back portion (61).

The base plate (60) of the body has a shape that is substantially similar to the stiffening plate (5), is rigid and indeformable. The base plate (60) has a perfectly smooth planar upper surface (68), which is intended to be faced towards the plantar area of the patient's foot.

The base plate (60) of the body (6) is fixed inside the cavity (50) of the stiffening plate (5) by means of snap-fit coupling.

With reference to FIG. 2, the base plate (60) of the body comprises a perimeter edge (62) that protrudes on top from the base plate (60) in such manner to define an upper housing (63).

The base plate (60) of the body comprises two elastically flexible back lateral tabs (65) ending with base teeth (65a) adapted to be fitted inside the back slots (52) obtained in the stiffening plate (5). The base plate (60) of the body also comprises two front teeth (66) that protrude frontally from the front part of the perimeter edge (62) of the base plate (60) of the body in order to be fitted in the front slots (58) of the stiffening plate (5).

The back portion (61) of the body is curved in cross-section and is provided with an upper border (61a) and lateral borders (61b). The back portion (61) of the body (6) has a concavity intended to be faced towards the calcaneus and towards the back part of the patient's tibia.

The brace (1) also comprises a flange (G) shaped as a square plate and connected to the back portion (61) of the body (6) by means of attachments (A) in order to protrude on the back of the body. The flange (G) is used for auxiliary treatments, for example to exercise a positive or negative pressure or to house a plantar pressure measuring device.

Holes (66) are obtained on the perimeter edge (62) of the base portion (60) and in the back portion (61) of the body, in proximity to the lateral borders (61b) of said back portion (61) of the body.

The brace (1) comprises a monolithic upper (7) molded from a soft thermoformable material, advantageously EVA. Said upper (7) has a net or grid structure with a dense series of through holes (76).

The upper (7) comprises a back portion (70) and two lateral portions (71).

The back portion (70) of the upper is curved in cross-section and has a concavity intended to be faced towards the patient's Achilles tendon, in such manner to surround the patient's calcaneus and the back part of the tibia.

In particular, the back portion (70) of the upper has a concavity that corresponds to the concavity of the back portion (61) of the body.

The lateral portions (71) of the upper (7) extend frontally from the back portion (70) in such manner to surround the internal side and the external side of the foot of the patient wearing the brace (1). The lateral portions (71) comprise a lower edge (72) and a plurality of wings (77) that protrude from the lower edge (72) of the lateral portions (71) towards the inside of the brace in order to be disposed on the upper surface (68) of the base plate (60) of the body, inside the upper housing (63) of the base plate (60) of the body.

The brace (1) comprises a soft intermediate sole (3) intended to be disposed inside the upper housing (63) of the base plate (60) of the body, above the wings (77) of the upper that remain therefore tightened between the intermediate sole (3) in upper position and the base plate (60) of the body in lower position, thus preventing the upper (7) from being freely extracted from the body (6). Evidently, said extraction can be easily and immediately made by simply removing the intermediate sole (3) from the upper (7).

Said intermediate sole (3) comprises three arch supports (31, 32, 33) with different elastic properties.

Figures 4, 5:
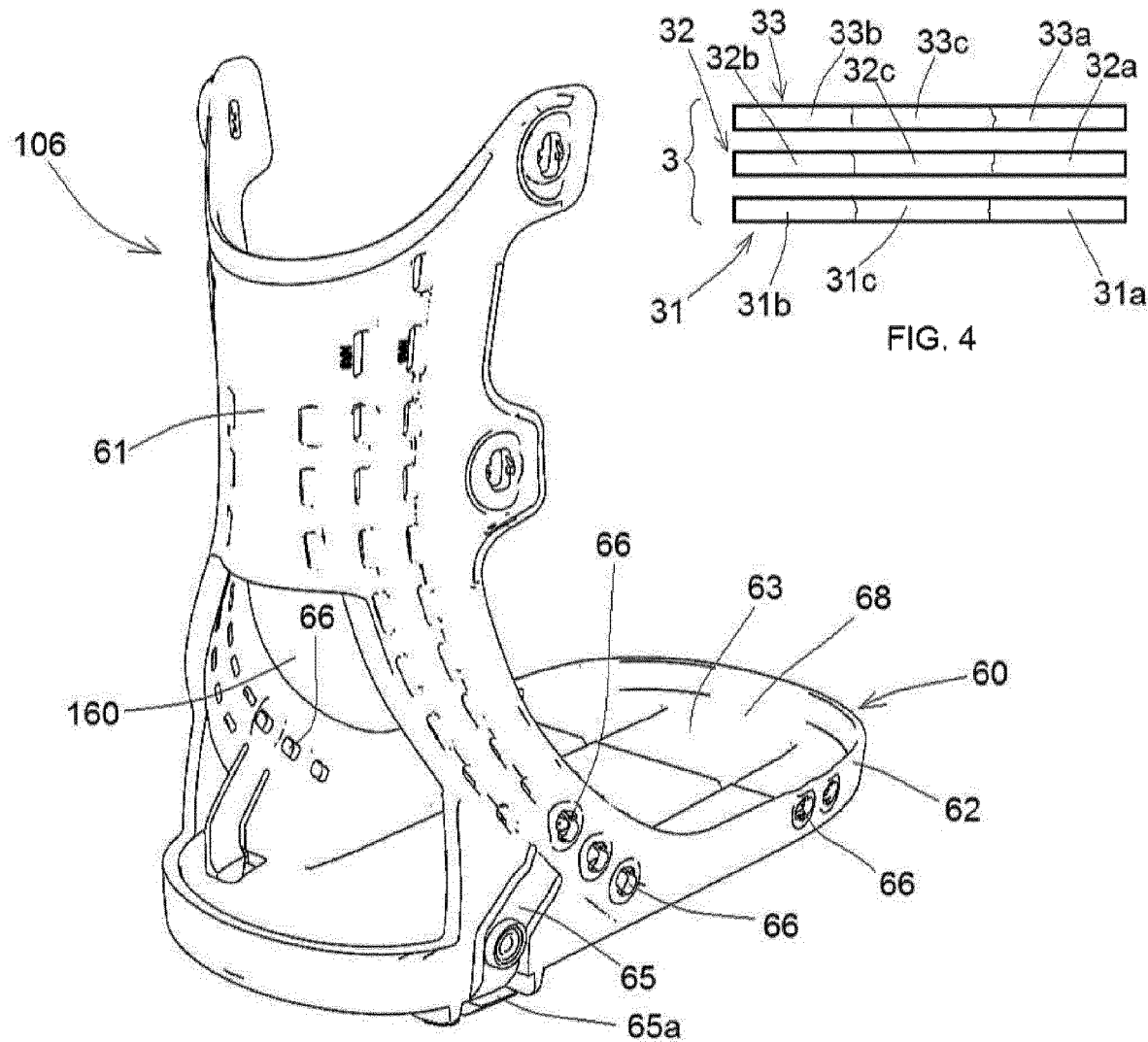
FIG. 4 is a cross-sectional view of the soft intermediate sole of the brace of the invention.
FIG. 5 is an axonometric view of a second embodiment of the body of the brace according to the invention.

With reference to FIG. 5, each arch support (31, 32, 33) of the intermediate sole (3) comprises:
a front portion (31a, 32a, 33a);
a back portion (31b, 32b, 33b); and
a central portion (31c, 32c, 33c).

The modular intermediate sole (3) allows for fixing the upper (7) with respect to the base plate (60) of the body and, at the same time, modifying the hardness and elasticity of the surface that supports the patient's foot according to the patient's requirements.

The upper (7) is connected to the body (6) by means of snap-fit coupling. In particular, the back portion (70) of the upper comprises two projections (74) disposed on the back and intended to be engaged inside openings (64) obtained in the back portion (61) of the body (6), as shown in FIGS. 1 and 2.

Moreover, the upper (7) is fixed to the body (6) on the upper edge (61a) of the back portion (61) of the body. In particular, the upper (7) comprises an upper neck (7b) and a beak (7a), which is obtained on the neck (7b) of the upper and is intended to be coupled with the upper edge (61a) of the back portion (61) of the body in such manner to fix the upper (7) to the body (6).

The brace (1) also comprises a tibial protection (8) with an L-shaped configuration in cross-section. The tibial protection (8) comprises a horizontal portion (80) intended to surround the dorsum of the patient's foot, and a vertical portion (81) intended to surround the patient's tibia.

The horizontal portion (80) and the vertical portion (81) of the tibial protection have a curved shape in cross-section and are provided with a concavity intended to be respectively faced towards the dorsum of the patient's foot and towards the patient's tibia.

The tibial protection (8) is made of the same material as the upper (7); in particular, the tibial protection (8) is a monolithic EVA piece with a net or grid structure, provided with a plurality of through holes (86).

It must be noted that the material and the structure of said tibial protection (8) allow the patient to cut said tibial protection in a suitable way to make it as comfortable as possible and associate it with the dorsum and the neck of the patient's foot.

With reference to FIGS. 1 and 2, the brace (1) comprises fixing means to fix the tibial protection (8) on the upper (7). Said fixing means advantageously comprise wings (9) with a semi-elliptical shape. Each wing (9) has a through hole (90) and a slot (91). Each wing (9) is revolvingly connected to the body (6) by means of pins (92) that are fitted in the through hole (90) of the wing (9) and in one of the holes (66) of the body.

Said fixing means also comprise straps (F) that are inserted and slide in the slots (91) of the wings to compress and hold the tibial protection (8) on the upper (7).

In view of the above, all the fixing means (9, 92, F) of the brace (1) can be removed and replaced according to the pathology and treatment of the patient's foot. In fact, to remove and replace the fixing means (9, 92, F), it is simply necessary to extract the pin (92) from one of the holes (66) of the body, move the wing (9) to another position and insert the pin (92) again in the through hole (90) of the wing and in another hole (66) of the body.

In this way the patient can choose the most comfortable fixing points for the straps (F) according to the position of the injuries on his foot.

FIG. 5 shows a second embodiment of a body (106) that is basically identical to the body (6) as described above, except for the fact that it is provided with a slot (160) obtained on the heel of the patient's foot to make it easier for the patient to insert his foot in the brace in case of a pathology that requires the heel to remain free. The body (106) can be connected to the stiffening plate (5) and to the upper (7) of the brace (1) with the same means and in the same way as described above for the body (6).

FIG. 6 shows a bottom (F2) using a sole (102) with a different profile compared to the one illustrated in FIG. 2, it being understood that also the bottom (F2) is provided with the stiffening plate (5) that allows to couple the bottom (F2) with the body by means of snap-fit coupling.

The sole (102) has a tread (121) comprising a front portion (121a), a back portion (121b) and a central portion (121c), disposed in correspondence with the Chopart's line of the foot, between the front portion (121a) and the back portion (121b) of the tread (121) of the bottom (102).

The front portion (121a) and the back portion (121b) of the tread (121) of the sole are convex and have the same concavity with the same preset radius of curvature.

The central portion (121c) of the tread (121) of the sole (102) has a higher radius of curvature than the front portion (121a) and the back portion (121b); preferably, the central portion (121c) of the tread (121) of the sole (102) is flat.

The central portion (121c) of the tread (121) of the sole (102) is very short compared to the front portion (121a) and the back portion (121b). The central portion (121c) of the tread (121) of the sole (102) has a length (L) lower than 15 mm, preferably comprised between 8 mm and 12 mm. The fact that the central portion (121c) of the tread (121) of the sole has a reduced length makes the brace unstable when the central portion (121c) of the tread (121) of the sole rests on the ground. Consequently, the deambulation of a patient wearing the brace (1) with the sole (102) implies a rolling motion of the sole (102) on the ground. The rolling motion provides for one of portions (121a, 121b, 121c) of the tread (121) of the sole to roll continuously and progressively on the ground. The progressive rolling motion of the sole (102) of the brace (1) allows for perfectly distributing the patient's weight on the entire surface of the sole (102) and avoids stress and trauma on the patient's foot.

The invention claimed is:

1. A brace comprising:
    a bottom having a sole, the sole being of a soft material and having a tread, the tread adapted to contact an underlying surface;
    a rigid body having a base plate, wherein said rigid body has a back portion protruding orthogonally from the base plate;
    a monolithic upper removably connected to said rigid body, wherein said monolithic upper has a plurality of wings protruding from a lower edge thereof and positioned on the base plate of said rigid body, the back portion having a curved cross-section and having a concavity facing toward a back portion of said monolithic upper; and
    at least one insole disposed on the base plate of said rigid body above the plurality of wings of said monolithic upper, said at least one insole being of a soft material, wherein said bottom has a stiffening plate of a non-deformable hard material, the stiffening plate being fixed on the sole, wherein the base plate of said rigid body is removably connected to the stiffening plate by a snap-fit coupling of teeth of said rigid body with slots of said stiffening plate, wherein said rigid body comprises:
        a plurality of front teeth protruding frontally from the base plate so as to engage into front slots in a frontal portion of the stiffening plate, said plurality of front teeth being located along a peripheral edge of the base plate; and
        a plurality of elastically flexible back lateral tabs ending with base teeth, the base teeth insertable into back slots of the stiffening plate, said plurality of elastically flexible back lateral tabs comprising first and second elastically flexible back lateral tabs positioned on opposing lateral sides of the base plate.

2. The brace of claim 1, wherein said monolithic upper is a single piece ethylene vinyl acetate (EVA) molding.

3. The brace of claim 1, wherein said monolithic upper has a grid structure with a plurality of holes.

4. The brace of claim 1, wherein said monolithic upper has a back portion and a pair of lateral portions that extend forwardly from the back portion of said monolithic upper, said monolithic upper adapted to surround an external side and an internal side of a human foot, the back portion of said monolithic upper having a concavity adapted to face an Achilles tendon of the human foot.

5. The brace of claim 4, said plurality of wings positioned along an entirety of lower edges of said pair of lateral portions.

6. The brace of claim 1, wherein the stiffening plate is glued to the sole.

7. The brace of claim 1, further comprising:
    a monolithic tibial protection formed of an ethylene vinyl acetate (EVA) material; and
    A fixing means removably fixing said tibial protection on said monolithic upper.

8. The brace of claim 7, wherein said tibial protection has a net structure having a plurality of holes.

9. The brace of claim 7, wherein said fixing means comprising:
    a plurality of wings hinged onto said rigid body, each of said plurality of wings having a slot; and
    a plurality of straps slidable in said plurality of slots of said plurality of wings so as to compress and hold said tibial protection on said monolithic upper.

10. The brace of claim 1, wherein the tread of the sole has a front portion, a back portion and a central portion adapted to be disposed so as to correspond with a Chopart line of the human foot, the front portion and the back portion being convex, the central portion having a radius of curvature greater than the radius of curvature of the front portion and the back portion, the central portion having a length less than 15 millimeters.

11. The brace of claim 1, wherein said rigid body has a slot adapted to correspond to a heel of the human foot.

* * * * *